United States Patent [19]

Mookherjee et al.

[11] Patent Number: 5,263,359
[45] Date of Patent: Nov. 23, 1993

[54] METHOD AND APPARATUS FOR SIMULTANEOUSLY ANALYZING AROMA EMITTED FROM THE INTERIOR AND EXTERIOR OF LIVING TREE AND OPTIONALLY FROM LIVING FRUIT

[75] Inventors: Braja D. Mookherjee, Holmdel; Robert W. Trenkle, Brielle; Subha M. Patel, Bridgewater; Sharon M. Brown, Fair Haven, all of N.J.

[73] Assignee: International Flavors & Fragrances Inc., New York, N.Y.

[21] Appl. No.: 23,966

[22] Filed: Feb. 26, 1993

Related U.S. Application Data

[63] Continuation-in-part of Ser. No. 988,337, Dec. 9, 1992.

[51] Int. Cl.$^5$ ............................................. G01N 31/00
[52] U.S. Cl. ................................. 73/23.34; 73/23.2
[58] Field of Search ............... 73/23.34, 23.2; 422/83, 422/98

[56] References Cited

U.S. PATENT DOCUMENTS

| | | | |
|---|---|---|---|
| 3,902,851 | 9/1975 | Dravnieks | 73/23.34 |
| 4,770,027 | 9/1988 | Ehara et al. | 73/23.34 |
| 4,884,435 | 12/1989 | Ehara | 73/23.34 |
| 5,136,805 | 8/1992 | Mookherjee et al. | 47/69 |
| 5,149,504 | 9/1992 | Tanaka | 73/23.34 |
| 5,177,994 | 1/1993 | Moriizumi et al. | 73/23.34 |

OTHER PUBLICATIONS

Mookherje et al., J. Ess. Oil. Res., vol. 2, pp. 85-90, (Mar./Apr. 1989), title "Live vs. Dead. Part II. A Comparative Analysis of the Headspace Volatiles of Some Important Fragrance and Flavor Raw Materials".

Primary Examiner—Hezron E. Williams
Assistant Examiner—Valerie D. Francies
Attorney, Agent, or Firm—Arthur L. Liberman

[57] ABSTRACT

A process for quantitatively and qualitatively substantially continuously analyzing the aroma emitted and rates of emission of the components thereof:
(I) from within the pit section and/or the inner wood section; and
(II) the outer bark surface of a living tree, simultaneously, and optionally from within and from the outer surface of one or more fruits borne by said living tree using simultaneously operating aroma trapping devices connected to the outer tree trunk surface and an inner location within the tree and, if desired, connected to the fruit surface and an internal location within the fruit. Also described is apparatus for carrying out such a process. The living tree, for example, may be a living Douglas Fir or a living Maple Tree or a living Papaya Tree or a living Mahogany Tree or a living Nectarine Tree.

7 Claims, 6 Drawing Sheets

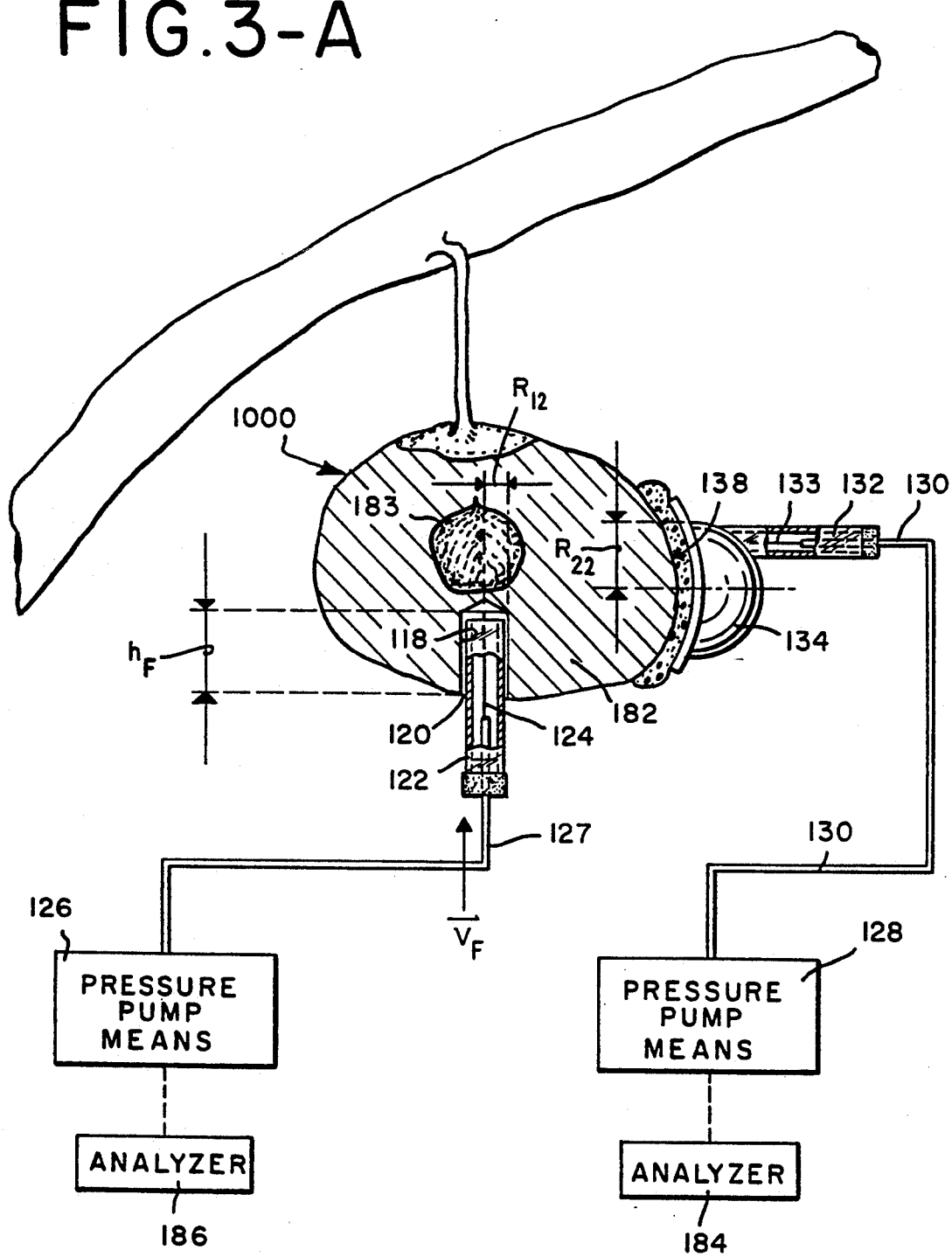
FIG.3-A

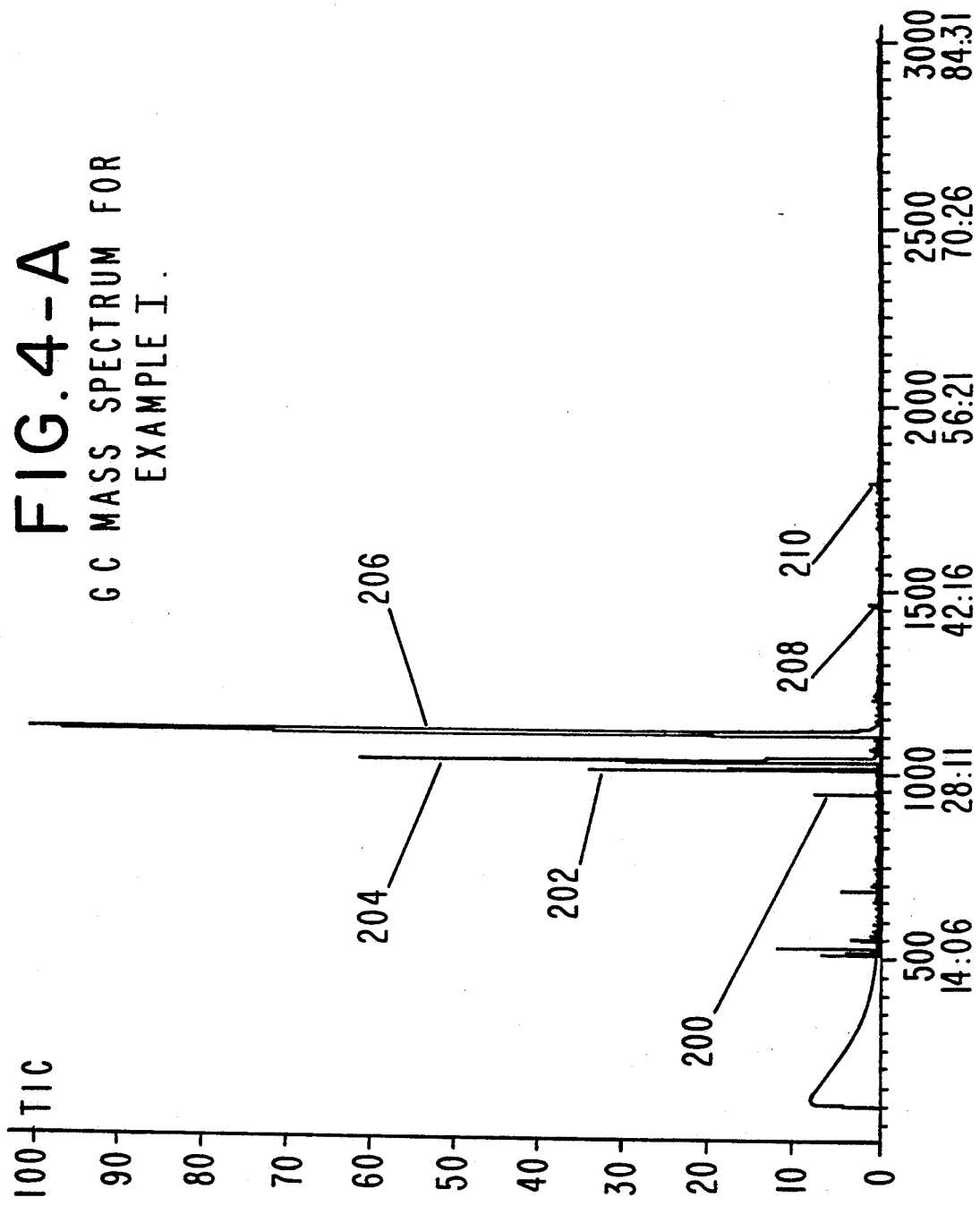

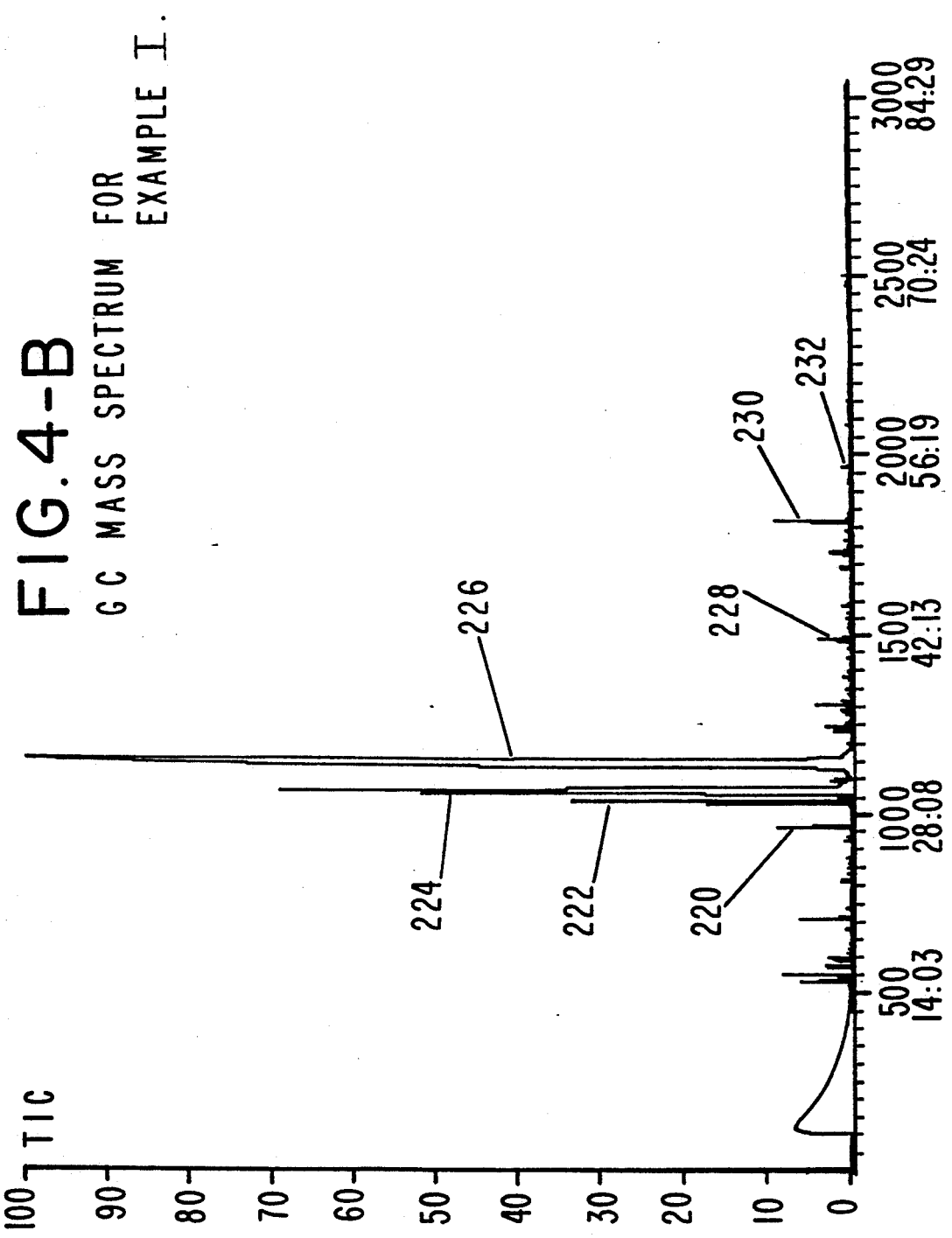

METHOD AND APPARATUS FOR SIMULTANEOUSLY ANALYZING AROMA EMITTED FROM THE INTERIOR AND EXTERIOR OF LIVING TREE AND OPTIONALLY FROM LIVING FRUIT

RELATED PATENT APPLICATIONS

This Application is a Continuation-in-Part of Application for U.S. Letters Patent, Ser. No. 988, 337 filed on Dec. 9, 1992.

BACKGROUND OF THE INVENTION

Our invention concerns a process for quantitatively and qualitatively substantially continuously analyzing the aroma emitted and rates of emission of the components thereof from within the inner wood section and/or the pith section and from the outer tree bark surface of a living tree simultaneously, and, optionally, from within and from the outer surface of one or more fruits borne by said living tree, simultaneously, and apparatus for carrying out such a process.

Uses of aromas evolved from the wood parts and the pith sections of living trees are highly sought after in the perfumery and flavor arts. Great difficulty has been experienced in attempting to capture and reproduce actual aroma ingredients of the wood parts and pith parts of the living tree at various points in time relevant to the maturation of the living tree.

U.S. Letters Pat. No. 5,136,805 issued on Aug. 11, 1992 describes an air-tight flexible transparent container containing at least one living flower immersed in an aqueous suspension. Described in U.S. Letters Pat. No. 5,136,805 is an article useful (i) for display purposes; and/or (ii) for analysis of the head space in the container above the living flower when the container is fitted with a tube effecting communication of the internal 3-space (internal volume) of the container with outside analytical means and/or (iii) for aromatizing the environment surrounding the container when the container is fitted with a wick effecting communication of the internal 3-space (internal volume) of the container with the environment surrounding the container. However, U.S. Letters Pat. No. 5,136,805 does not teach or infer a technique for quantitatively and qualitatively substantially continuously analyzing the aroma emitted and rates of emission of the components thereof from within and from the outer bark surface of the woody or pithy parts of a living tree simultaneously, and optionally, from within and from the outer surface of one or more fruits borne by said living tree simultaneously.

SUMMARY OF THE INVENTION

Our invention is drawn to a process for quantitatively and qualitatively substantially continuously analyzing the aroma emitted and rates of emission of the components thereof:

(i) from within the inner wood section and/or pith section; and (ii) from the outer tree bark surface of one or more woody parts of a living tree simultaneously, and, optionally, quantitatively and qualitatively substantially continuously analyzing the aroma emitted and rates of emission of the components thereof:

(i') from within; and (ii') from the outer surface of one or more living fruits borne by said living tree.

Examples of such living trees are living Douglas Fir, living Texas Cedarwood trees, living Virginia Cedarwood trees, living Cherry trees, living Mahogany trees, living Nectarine trees, living Papaya trees, and living Maple trees. Examples of living Nectarine trees are those such as the Red Jewel Nectarine tree (disclosed and claimed in U.S. Plant Pat. No. 8,013 issued on Oct. 27, 1992) and the Red Diamond Nectarine tree (disclosed and claimed in U.S. Plant Pat. No. 3,165). The specifications of U.S. Plant Pat. Nos. 3,165 and 8,013 are incorporated by reference herein.

Our process comprises the steps of:

(a) removing a cylindrical core section from a section of one or more wood parts and/or the pith part of the living tree to form one or more core voids;

(b) placing a first trapping tube (connected to a vacuum pump) into the core void(s);

(c) applying an enclosure containing a second trapping tube (connected to a vacuum pump) to a portion of unbroken tree bark surface of the same living tree in a sealably affixable manner;

(d) engaging both vacuum pumps; and (e) analyzing the substances trapped in the trapping tubes on a substantially continuous basis; and, optionally:

(a') removing a cylindrical core section from a section of one or more living fruits borne by said living tree to form one or more core voids;

(b') placing a third trapping tube (connected to a vacuum pump) into the core void(s);

(c') applying an enclosure containing a fourth trapping tube (connected to a vacuum pump) to a portion of unbroken surface of the same living fruit in a sealably affixable manner;

(d') engaging both vacuum pumps; and (e') analyzing the substances trapped in the trapping tubes on a substantially continuous basis.

Thus, our invention also contemplates the multiple ongoing simultaneous analysis of (a) the inner and outer sections of a living tree and (b) the inner and outer sections of living fruit growing on said living tree (as is the case of a nectarine growing on a nectarine tree) according to the process disclosed and claimed in copending application for U.S. Lettes Patent Ser. No. 988,337 filed on Dec. 9, 1992 the specification for which is incorporated herein by reference.

Apparatus for carrying out such processes is also intended to be a part of our invention.

DETAILED DESCRIPTION OF THE INVENTION

Our invention covers a process for quantitatively and qualitatively substantially continuously analyzing the aroma emmited and rates of emission of the components thereof:

(i) from within the inner wood section and/or pith section; and (ii) from the outer tree bark surface of one or more wood parts (e.g., the main trunk) of a living tree simultaneously, and, optionally, quantitatively and qualitatively substantially continuously analyzing the aroma emmited and rates of emission of the components thereof:

(i') from within; and
(ii') from the outer surface of
one or more living fruits borne by said living tree simultaneously, consisting essentially of the steps of:
  (a) providing a living tree located on a given central axis having an outer tree bark surface, a substantial portion of which is located at a given distance from the central trunk or tree limb axis and an inner volume including an inner heartwood section or an inner sapwood section and in a number of instances an inner pith volume surrounding said central axis and encompassed by said outer tree bark surface;
  (b) removing a depth core section from said inner volume running from said outer tree bark surface to a depth of from about halfway up to entirely to the central trunk or tree limb axis, into said inner volume along a directional vector extending substantially radially from said central axis to said outer tree bark surface within said inner volume;
  (c)-1 providing first analytical apparatus means comprising a first trapping tube means attached to first negative pressure pump means associated with first chemical analysis means (e.g., GC-mass spectral, nuclear magnetic resonance, Raman spectral and infrared analytical equipment);
  (c)-2 providing second analytical apparatus means comprising a second trapping tube means attached to second negative pressure pump means associated with second chemical analysis means;
  (d) providing a hollow flexible enclosure means (e.g., a spherical cup-like enclosure) having an inner enclosure means void and an outer enclosure means surface encompassing said void and terminating at an enclosure rim means, said void being defined by said outer enclosure means surface and said enclosure rim means, an insertion orifice extending from said outer enclosure means surface to said inner enclosure means void, said enclosure means being capable of sealably gripping an unbroken portion of said outer tree bark surface of said living tree at said enclosure rim means;
  (e) causing said enclosure means to sealably grip said portion of said outer tree bark surface of said living tree at said enclosure rim means;
  (f) inserting said first trapping tube means into said core section void along said directional vector;
  (g) inserting said second trapping tube means through said insertion orifice causing it to be extended into said enclosure means void;
  (h) simultaneously engaging said first negative pressure pump means and said second pressure pump means whereby components of the aroma evolving from said outer tree bark surface of said living tree are entrapped in said second trapping tube means and components of the aroma evolving from within the pith and/or wood section of said living tree are entrapped in said first trapping tube means, simultaneously; and
  (j) analyzing the contents of said first trapping tube means using said first chemical analysis means and said second trapping tube means using said second chemical analysis means substantially continuously and substantially simultaneously; and
optionally, simultaneously:
  (a') providing one or more living fruits borne by said living tree each of which fruits is located on a given central axis having an outer surface, a substantial portion of which is located at a given distance from the central axis and an inner volume surrounding said central axis and encompassed by said outer surface;
  (b') removing a depth core section from said inner volume running from said outer surface to a depth of from about halfway up to entirely to the central axis into said inner volume along a directional vector extending substantially radially from said central axis to said outer surface within said inner volume;
  (c)-1: providing third analytical apparatus means comprising a third trapping tube means attached to third negative pressure pump means associated with third chemical analysis means (e.g, GC-mass spectral, nuclear magnetic resonance, Ramon spectral and infrared analytical equipment);
  (c)-2: providing fourth analytical apparatus means comprising a fourth trapping tube means attached to fourth negative pressure pump means associated with fourth chemical analysis means;
  (d') providing a hollow flexible enclosure means (e.g., a spherical cup-like enclosure) having an inner enclosure means void and an outer enclosure means surface encompassing said void and terminating at an enclosure rim means, said void being defined by said outer enclosure means surface and said enclosure rim means, an insertion orifice extending from said outer enclosure means surface to said inner enclosure means void, said enclosure means being capable of sealably gripping an unbroken portion of said outer surface of said living fruit at said enclosure rim means;
  (e') causing said enclosure means to sealably grip said portion of said outer surface of said living fruit at said enclosure rim means;
  (f') inserting said third trapping tube means into said core section void along said directional vector;
  (g') inserting said fourth trapping tube means through said insertion orifice causing it to be extended into said enclosure means void;
  (h') simultaneously engaging said third negative pressure pump means and said fourth negative pressure pump means whereby components of the aroma evolving from said outer surface of said living fruit are entrapped in said fourth trapping tube means and components of the aroma evolving from within said living fruit are entrapped in said third trapping tube means, simultaneously; and
  (j') analyzing the contents of said third trapping tube means using said third chemical analysis means and said fourth trapping tube means using said fourth chemical analysis means substantially continuously and substantially simultaneously.

Examples of various trees both fruit bearing and non-fruit bearing which are the subjects of our invention are as follows:
(i) the Douglas Fir (*Psoudotsuga taxifolia* (Lamb.) Britt;
(ii) the Papaya tree (*Carica Papaya*);
(iii) the Coconut Palm tree (*Cocos nucifera*);
(iv) the Texas Cedarwood (*Thuja plicata*);
(v) the Mahogany tree (*Swietenia candollea*);
(vi) the Wild Guyana Sandalwood tree;
(vii) the East Indian Sandalwood tree;
(viii) the Nectarine tree (the Red Jewel Nectarine tree and the Red Diamond Nectarine tree).

Thus, for example, in the case of a living Douglas Fir tree having an average trunk outside diameter of 8", the depth core would be about ¼" in diameter and the tube entering the core containing trapping material would be approximately 3/16" in diameter and about 4" in length. Enclosed within the surrounding tube would be a trap such as a TENAX ® trap which would be ⅛" in diameter and 3.5" in length, for example.

When carrying out our process involving a living tree and one or more living fruits borne by said living tree, when the living fruit is one that has a pit such as a peach or a nectarine or a plum, then obviously the depth core can only extend to the outer surface of the pit and preferably the depth core (with respect to the living fruit) should extend about two-thirds of the way into the fruit without touching the surface of the pit. Thus, for example, in the case of a nectarine the depth core would be about a ¼" in diameter and the tube entering the core containing the trapping material would be approximately 3/16" in diameter and about 0.75" in length. Enclosed within the surrounding tube would be a trap such as a TENAX ® trap which would be ⅛" in diameter and 0.7" in length, for example.

Thus, various trapping materials are useful in the practice of our invention in both the trap used in trapping the materials emitted from within the inner wood section and/or pith section of the living tree and entrapping the materials emitted from the outer tree bark surface of the living tree. As stated, supra, TENAX ® is a preferable material. Various forms of TENAX ® are useful, for example, TENAX ®-GC. TENAX ® is a registered trademark of ENKA N.V. of The Kingdom of The Netherlands (CAS Registration No. 2438-68-9). Various forms of TENAX ® and methods of producing such forms of TENAX ® are described in the following U.S. Letters Patent, the disclosures of which are incorporated herein by reference:

U.S. Pat. No. 3,400,100 issued on Sep. 3, 1968 ("Process For The Preparation Of Polyphenylene Ethers")

U.S. Pat. No. 3,644,227 issued on Feb. 22, 1972 ("Separation Of Poly(2,6-Dimethyl-1,4-Phenyleoxide") from its blends with other polymers))

U.S. Pat. No. 3,703,564 issued on Nov. 21, 1972 (Bis[-Polyphenyleneoxide]-Ester Block Copolymers")

U.S. Pat. No. 4,431,779 issued on Feb. 14, 1984 ("Polyetheramide-Polyphenylene Ether Blends")

U.S. Pat. No. 4,801,645 issued on Jan. 31, 1989 ("Thermoplastic Resin Composition")

TENAX ®-GC is actually a polyphenyleneoxide defined according to the structure:

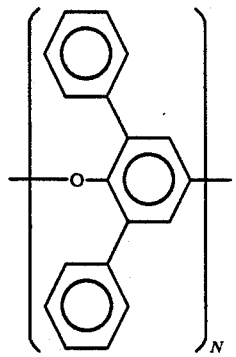

wherein N is an integer of from about 100 up to about 150.

Other trapping materials useful in the practice of our invention are as follows: Activated Carbon marketed by Aldrich Chemical Company of 1001 West Saint Paul Avenue, Milwaukee, Wis. 53233 (Catalog Nos. 16, 155-1; 29, 259-1; 24, 223-3; 24, 224-1 and 24, 227-6); Activated Alumina marketed by Sigma Chemical Company of St. Louis, Mo. (Catalog Nos. A8753; A8878; A9003; A1772; A1522 and A2272); Silica Gels marketed by Sigma Chemical Company, for example, Catalog Nos. S4004; S6628 and H8506; CHROMOSORB ® (registered trademark of the Johns-Manville Company of Manville, N.J.) such as CHROMOSORB ® such as LC-1; CHROMOSORB ® LC-2; CHROMOSORB ® LC-3, and CHROMOSORB ® LC-7 marketed by the Sigma Chemical Company under Catalog Nos. C 0641; C 0766, C 5517 and C 6269.

The negative pressure pump means of our invention is preferably a vacuum pump of the "Low Flow" variety, for example, "Low Flow" pumps marketed by the Ametek Company of Largo, Fla. 34643 (the Ametek Constant Flow Sampler).

Examples of other trees amenable to the practice of our invention are as follows:

(i) the Green Ash Tree named "Cimmzam" disclosed and claimed in U.S. Plant Pat. No. 8,077, granted on Dec. 29, 1992 (the specification for which is incorporated herein by reference);

(ii) the Prima Black Plum 5-25 Tree disclosed and claimed in U.S. Plant Pat. No. 8,067 granted on Dec. 22, 1992 (the specification for which is incorporated herein by reference);

(iii) the Prima Black Plum 8-15 Tree disclosed and claimed in U.S. Plant Pat. No. 8,068 granted on Dec. 22, 1992 (the specification for which is incorporated herein by reference);

(iv) the Plum Tree "Green Jade" disclosed and claimed in U.S. Plant Pat. No. 8,069 granted on Dec. 22, 1992, (the specification for which is incorporated herein by reference);

(v) the Peach Tree "Summer Sweet" disclosed and claimed in U.S. Plant Pat. No. 8,070 granted on Dec. 22, 1992, (the specification for which is incorporated herein by reference); and (vi) the Peach Tree "Compact Flavorette" disclosed and claimed in U.S. Plant Pat. No. 8,071 granted on Dec. 22, 1992, (the specification for which is incorporated herein by reference).

(i) from within; and
(ii) from the outer tree bark surface
of the living tree simultaneously.

Figure 2:
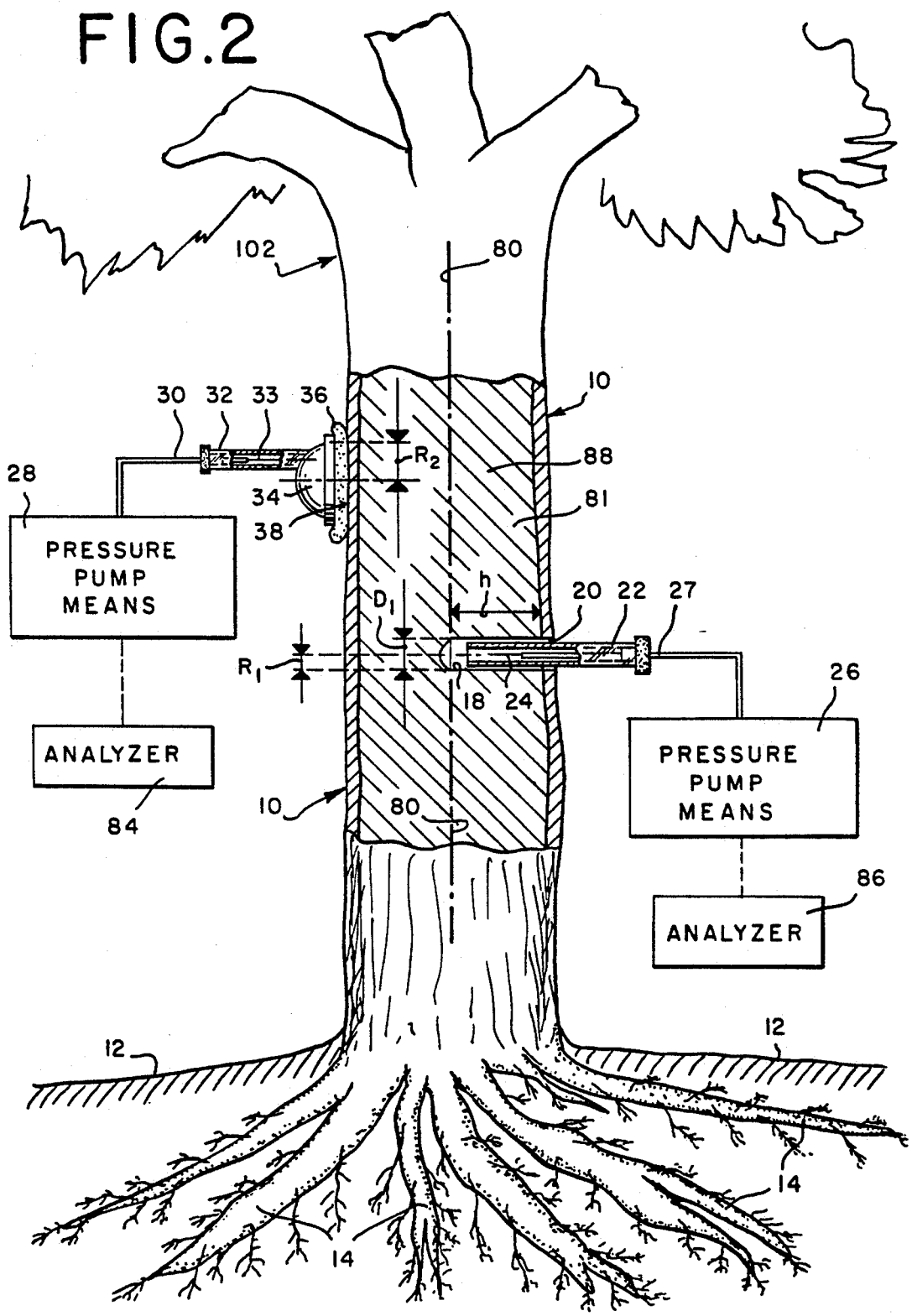
Figure 3:
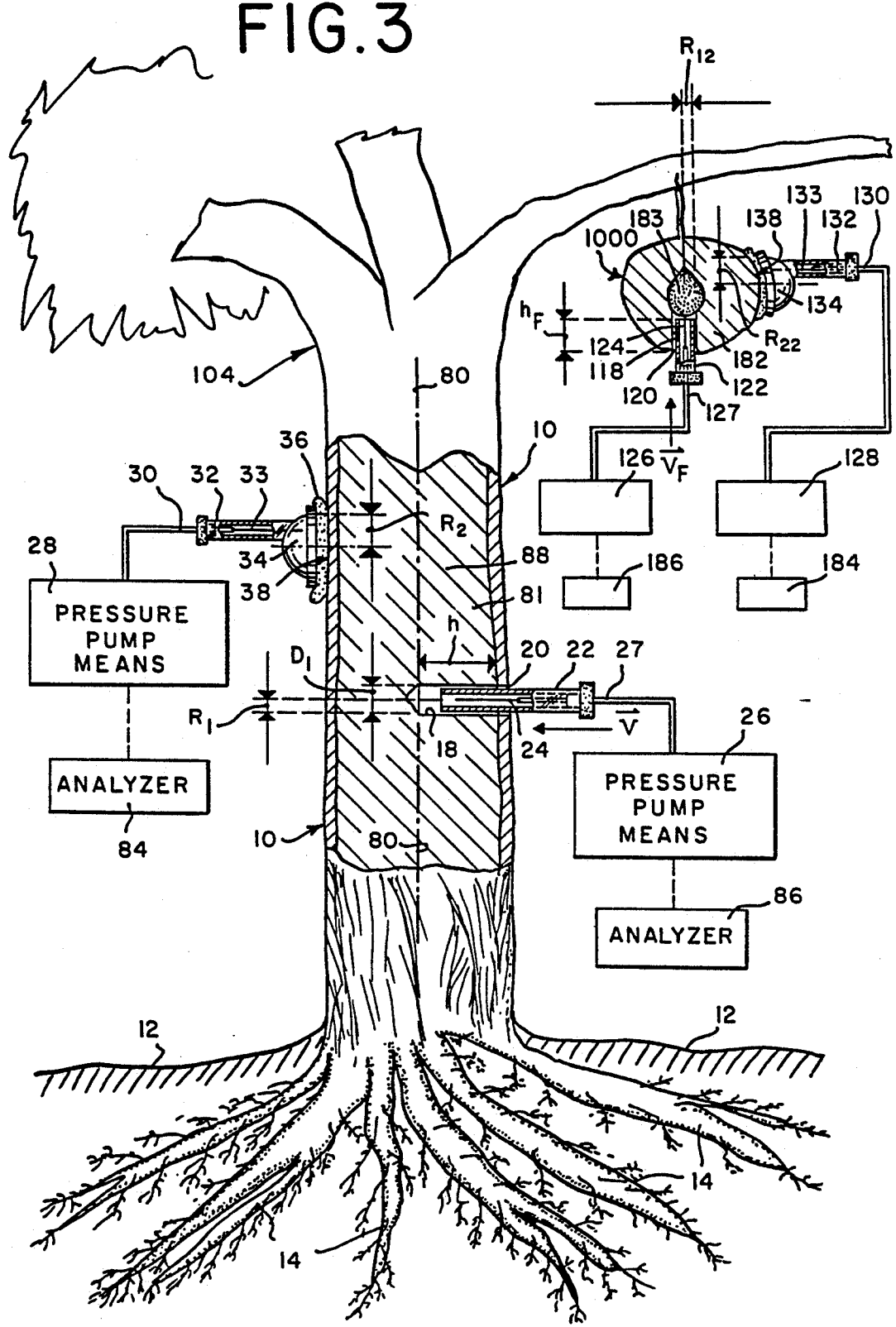

FIG. 2 is a schematic drawing showing a cut-away side elevation view of the wood part (without the presence of a pith section) of a living tree (without bearing any living fruit) being quantitatively and qualitatively substantially continuously analyzed for the aroma emitted and rate of emission of the components thereof:

(i) from within; and
(ii) from the outer tree bark surface
of the living tree simultaneously FIG. 3 is a schematic drawing showing a cut-away side elevation view of the wood part of a living tree bearing living fruit being quantitatively and qualitatively substantially continuously analyzed for the aroma emitted and rate of emission of the components thereof:
 (i) from within; and
 (ii) from the outer tree bark surface
of the living tree and, simultaneously:
 (i') from within; and
 (ii') from the outer surface
of the living fruit borne on said living tree simultaneously.

FIG. 3A is a detailed schematic drawing showing a cut-away side elevation view of a living fruit borne on the living tree of FIG. 3, said living fruit being quantitatively and qualitatively substantially continuously analyzed for the aroma emitted and rate of emission of the components thereof:
 (i) from within; and
 (ii) from the outer surface
of the living fruit simultaneously.

FIG. 4A is the GC mass spectrum of the composition of the aroma produced by carrying out Example I, infra, of the interior of a living Douglas Fir tree using the apparatus of FIG. 2.

FIG. 4B is the GC mass spectrum of the aroma emitted from the external surface of a living Douglas Fir tree in Example I, infra, using the apparatus shown in FIG. 2.

DETAILED DESCRIPTION OF THE DRAWINGS

Figure 1:
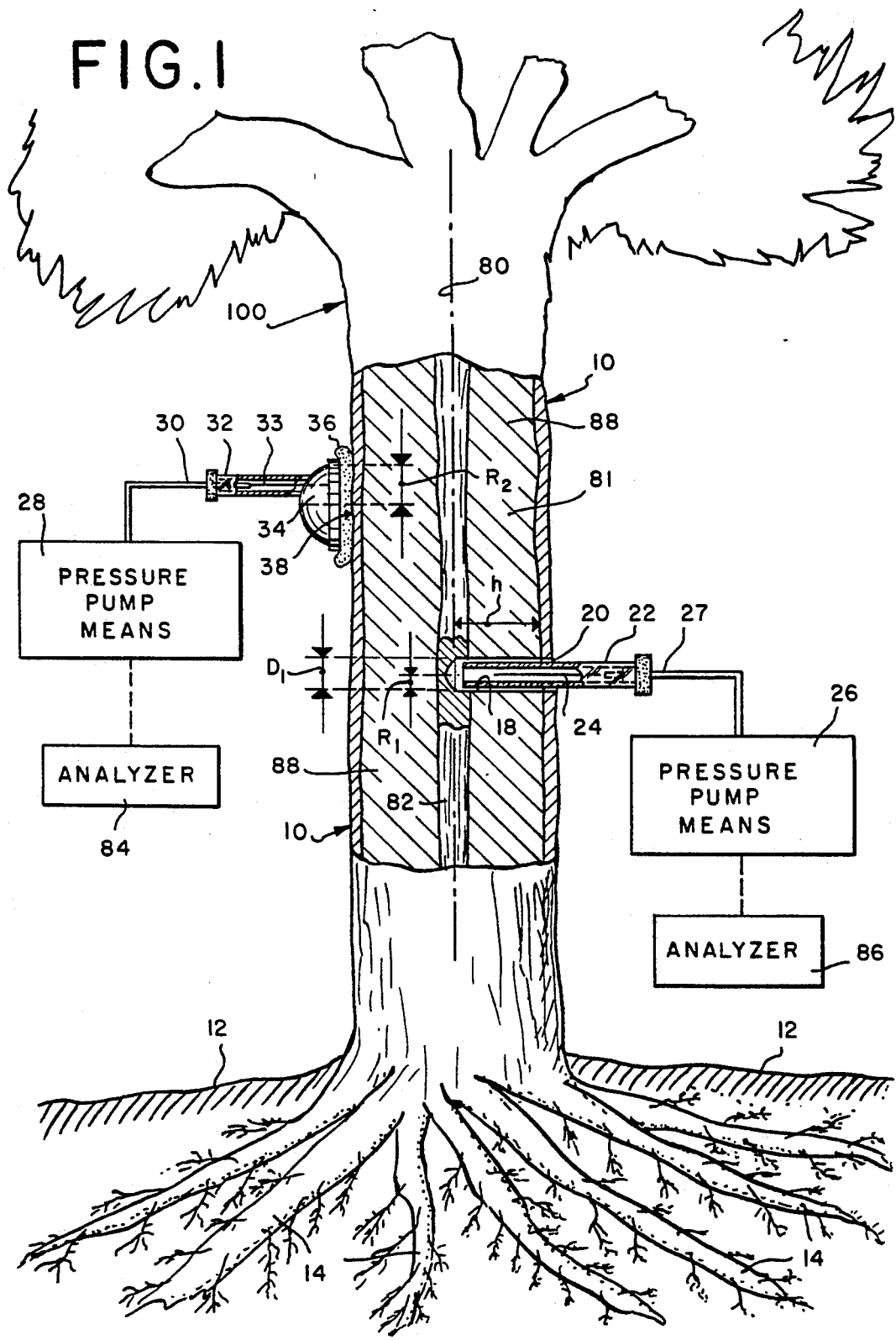
FIG. 1 is a schematic drawing showing a cut-away side elevation view of the wood and pith portions of a living tree (without bearing any living fruit) being quantitatively and qualitatively substantially continuously analyzed for the aroma emitted and rate of emission of the components thereof.

Referring to FIG. 1, a living tree having its axis 80 and roots 14 living in ground 12 having an inner volume 81, inner wood volume 88 and pith volume 82 and a tree bark surface 10 is shown having the aroma and rate of emission of the components thereof:
 (i) from within the inner pith section of the living tree; and
 (ii) from the outer tree bark surface
of the living tree being analyzed simultaneously.

A substantial portion of the outer tree bark surface 10 is located at a given distance "h" (e.g., 4") from the central axis 80, and an inner pith volume 82 surrounds the central axis 80 and is encompassed by the wood section 88 surrounding the pith volume 82 and outer surface 10; and a depth core section 18 is removed from the inner volume 81 including part of the inner wood volume 88 and pith volume 82 along a directional vector "V" extending substantially radially from the central axis 80 to the outer tree bark surface 10 within the inner volume 81 including the pith volume 82. The depth core section 18 has an effective diameter $D_1$ (e.g., about $\frac{1}{4}$") equal to $2\times$(the effective radius, $R_1$/(about $\frac{1}{8}$")) and a core section volume ranging from about $$[\pi R_1^2 h]$$

down to about $$\left[\frac{\pi R_1^2 h}{2}\right]$$

thereby forming a core section void within the living tree. First analytical apparatus means in FIG. 1 comprises a first trapping tube means (22, 24) which is a glass outer tube 22 and a trapping tube 24 inserted through opening 20 into depth core 18. Attached to the trapping tube 24 (which may, for example, contain TE-NAX ®-GC) is tube 27 connected to a negative pressure pump means 26 ("first negative pressure pump means").

Reference numeral 86 represents analytical apparatus capable of providing GC-mass spectra of the trapped substance which may be taken further together with spectral apparatus capable of providing infrared spectra of the trapped substance, spectral apparatus capable of providing NMR spectra of the trapped substance and spectral apparatus capable of providing Raman spectra of the trapped substance. The analytical apparatus represented by reference numeral 86 is also herein referred to as "first analyzer means".

Second analytical apparatus means for analyzing the aroma emitted from the tree bark surface of the living tree of FIG. 1 comprises second trapping tube means 32-33 (outer tube 32 encompassing inner trapping tube 33) inserted into enclosure 34 which is sealably affixed at 36 to a portion of the tree bark surface 38 of the living tree 100. The trapping tube means is connected to tube 30 which is connected to negative pressure pump 28 ("second negative pressure pump means") associated with analyzer 84 ("second analyzer means")(e.g., GC-mass spectral analyzer; Raman spectral analyzer; nuclear magnetic resonance analyzer; and infrared analyzer). The apparatus is maintained in place in conjunction with the living tree, e.g., the living tree of FIG. 1. The trapping tube is inserted into the enclosure means (e.g., a hemispherically-shaped cup means having an inner cup means void and an outer cup means surface surrounding the void and terminating at a substantially circular rim of radius $R_2$ with the inner volume of said cup means being about:

$$[\tfrac{2}{3}\pi R_2^3].$$

Thus, when the first negative pressure pump means 26 and the second negative pressure pump means 28 are simultaneously engaged, the components of the aroma evolving from the outer tree bark surface of the living tree (e.g., the living tree shown by reference numeral 100) are entrapped in the second trapping tube means inner trapping tube 33 and the first trapping tube means inner trapping tube 24 simultaneously, enabling the contents of the first trapping tube means 22-24 and the second trapping tube means 32-33 to be continuously analyzed substantially simultaneously using first and second chemical analysis means 86 and 84, respectively.

Referring to FIG. 2, a living tree (e.g., a Douglas Fir) having axis 80 and roots 14 living in ground 12 having an inner volume 81 and inner wood volume 88 and a tree bark surface 10 is shown having the aroma and rate of emission of the components thereof:
 (i) from within the inner wood section of the living tree; and
 (ii) from the outer tree bark surface
of the living tree being analyzed simultaneously.

A substantial portion of the outer tree bark surface 10 is located at a given distance "h" (e.g. 4") from the central axis 80 and an inner volume 88 surrounds the central axis 80 and is encompassed by the wood section 88 and the outer tree bark surface 10; and a depth core section 18 is removed from the inner volume 81 including part of the inner wood volume 88 along a directional vector "V" extending substantially radially from the central axis 80 to the outer tree bark surface 10 within the inner volume 81. The depth core section 18 has an effective diameter $D_1$ (e.g., about $\frac{1}{4}''$) equal to $2\times$(the effective radius, $R_1$ (about $\frac{1}{8}''$)) and a core section volume ranging from about $$[\pi R_1^2 h]$$

down to about $$\left[\frac{\pi R_1^2 h}{2}\right]$$

thereby forming a core section void within the living tree. First analytical apparatus means in FIG. 2 comprises a first trapping tube means (22, 24) which is a glass outer tube 22 and an inner trapping tube 24 inserted through opening 20 into depth core 18. Attached to the trapping tube 24 (which may, for example, contain TENAX®-GC) is tube 27 connected to a negative pressure pump means 26. Reference numeral 86 represents analytical apparatus capable of providing GC-mass spectra of the trapped substance which may be taken further together with spectral apparatus capable of providing infrared spectra of the trapped substance and spectral apparatus capable of providing NMR spectra of the trapped substance.

Second analytical apparatus means (for analyzing the aroma emitted from the surface of the living tree of FIG. 2) comprises second trapping tube means 32 inserted into enclosure 34 which enclosure is sealably affixed at 36 to the portion of the tree bark surface of the living tree, 38. The trapping tube means is connected to tube 30 which is connected to negative pressure pump 28 associated with analyzer 84 (e.g., GC-mass spectral analyzer; nuclear magnetic resonance analyzer; and infrared analyzer). The apparatus is maintained in place in conjunction with the living tree, e.g., the living tree of FIG. 2. The trapping tube is inserted into the enclosure means (e.g., a hemispherically-shaped cup means having an inner cup means void and an outer cup means surface surrounding the void and terminating at a substantially circular rim of radius $R_2$ with the inner volume of said cup means being about:

$$[\tfrac{2}{3}\pi R_2^3],$$

Thus, when the first negative pressure pump means 26 and the second negative pressure pump means 28 are simultaneously engaged, components of the aroma evolving from the outer tree bark surface of the living tree (e.g., the living tree shown by reference numeral 102) are entrapped in the second trapping tube means 32 and the first trapping tube means 22 simultaneously, enabling the contents of the first trapping tube means and the second trapping tube means to be continuously analyzed substantially simultaneously using the first and second chemical analysis means 86 and 84, respectively.

Referring to FIGS. 3 and 3A, living fruit 1000 borne on living tree 104 having inner volume 182 and containing pit 183 is shown having the aroma and rate of emission of the components thereof:

(i) from within the living fruit; and
(ii) from the outer surface of the living fruit being analyzed simultaneously with the analysis of the aroma of the inner volume 88 of the living tree 104 and the tree bark surface 10 of the living tree 104 of FIG. 3.

A substantial portion of the outer surface of living fruit 1000 is located at a given distance "$h_F$" (e.g., 0.75") from the central axis and an inner volume surrounds the central axis and is encompassed by the outer surface; and a depth core section 118 is removed from the inner volume 182 along a directional vector "$V_F$" extending substantially radially from the central axis to the outer surface of the living fruit within the inner volume 182. The depth core section 118 has an effective diameter $$2R_{12}$$

(e.g., about $\frac{1}{4}''$) equal to $2\times$(the effective radius $R_{12}$ (about $\frac{1}{8}''$)) and a core section volume ranging from about $$[\pi R_{12}^2 h_F]$$

down to about $$\left[\frac{\pi R_{12}^2 h_F}{2}\right]$$

thereby forming a core section void within the living fruit. Third analytical apparatus means in FIG. 3 comprises a third trapping tube means (122, 124) which is an outer glass tube 122 and an inner trapping tube 124 inserted through opening 120 into depth core 118. Attached to the trapping tube 124 (which may, for example, contain TENAX®-GC) is tube 127 connected to third negative pressure pump means 126. Reference numeral 186 represents analytical apparatus capable of providing GC-mass spectra of the trapped substance which may be further taken together with spectral apparatus capable of providing infrared spectra of the trapped substance and spectral apparatus capable of providing NMR spectra of the trapped substance. The apparatus represented by reference numeral 186 is also hereinafter referred to as "third analyzer means".

Fourth analytical apparatus means (for analyzing the aroma emitted from the surface of the living fruit of FIG. 3) comprises fourth trapping tube means 132, 133 inserted into enclosure 134 which enclosure is sealably affixed on surface 138 of the living fruit. The trapping tube means is connected to tube 130 which is connected to negative pressure pump 128 ("fourth negative pressure pump means") associated with analyzer 184 ("fourth analyzer means")(e.g., GC-mass spectral analyzer; nuclear magnetic resonance analyzer; and infrared analyzer). The apparatus is maintained in place in conjunction with the living fruit, e.g., the living fruit shown in FIG. 3 having pit 183 contained therein. The trapping tube 130 is inserted into the enclosure means (e.g., a hemispherically-shaped cup means having an inner cup means void 134 and an outer cup means surface surrounding the void 134 and terminating at a substantially circular rim of radius $R_{22}$ with the inner volume of said cup means being about:

$$[\tfrac{2}{3}\pi R_{22}^3],$$

Thus, when the third negative pressure pump means 126 and the fourth negative pressure pump means 128 are simultaneously engaged, the components of the aroma evolving from the outer surface of the living fruit 1000 are entrapped in the fourth trapping tube means 132 and the third trapping tube means 122 simultaneously, enabling the contents of the third trapping tube means and the fourth trapping tube means to be continuously analyzed using said third and fourth chemical analysis means 186 and 184, respectively. Simultaneously, trapping tube means 24 and 33 enable the analysis by analyzers 86 and 84 to take place of the aroma components of the inner wood section 88 of tree 104 and of the outer bark surface section 38 of tree 104, respectively.

The detailed description of FIGS. 4A and 4B is set forth in the description of Example I, infra.

Thus, the following Example I is illustrative of our invention but our invention is only limited by the scope of the claims following said example.

EXAMPLE I

Head Space Sampling and the Analysis of the Interior and Exterior of a Living Tree

Objective

To analyze the head space of the exterior and interior of a living Douglas Fir tree to determine, through GC/MS analysis, the difference between the interior and exterior volatile head space constituents.

Procedure

A mature Douglas Fir tree approximately 18 feet tall and 8 inches in diameter at the base was chosen for headspace sampling and is the subject of the instant investigation.

A ¼ inch hole was drilled half way through the base of the tree to a depth of approximately 4 inches. A glass tube 5 inches×¼ inch outer diameter was then inserted 3.5 inches into the drilled-hole of the tree. A ⅛ inch diameter×4 inch long TENAX ® headspace trap was then placed into the hollow glass tube that was inserted into the tree. An alpha-2 pump (vacuum pump) was then attached to the trap and sampling begun.

Simultaneously, a clear spot was chosen opposite the interior sampling port at the base of the tree. A 25 ml ×½ inch clam shell headspace sampling apparatus was wired to the base of the tree.

Odorless tissue was stuffed around the glass clam shell apparatus where it touched the tree to insure a good seal. A TENAX ® headspace trap was inserted into the glass apparatus and was attached to a second alpha-2 pump. Both pumps were engaged simultaneously causing a flow rate of air through the traps of 40 ml/min. The pumps were operated for a period of seven hours. At the end of the seven hour period, the pumps' operation was terminated and the traps were opened and contents analyzed. The contents of the traps were analyzed by GC-MS analysis using a 50 M ×0.32 mm OV-2 fused silica column having conditions: 50°–220° C. at 3° C. per minute).

FIG. 4A is the GC-mass spectrum for the interior (sap wood) section of the Douglas Fir. The peak indicated by reference numeral 200 is the peak for alpha-pinene. The peak indicated by reference numeral 202 is the peak for beta-pinene. The peak indicated by reference numeral 204 is the peak for myrcene. The peak indicated by reference numeral 206 is the peak for limonene. The peak indicated by reference numeral 208 is the peak for thymol methyl ether. The peak indicated by reference numeral 210 is the peak for longifolene.

FIG. 4B is the GC-mass spectrum for the exterior headspace as indicated to be trapped, supra. The peak indicated by reference numeral 220 is the peak for alpha-pinene. The peak indicated by reference numeral 222 is the peak for beta-pinene. The peak indicated by reference numeral 224 is the peak for myrcene. The peak indicated by reference numeral 226 is the peak for limonene. The peak indicated by reference numeral 228 is the peak for thymol methyl ether. The peak indicated by reference numeral 230 is the peak for longifolene. The peak indicated by reference numeral 232 is the peak for a bisabolene isomer.

The entrapped interior and exterior Douglas Fir tree headspace analysis is set forth in detail as follows:

| Compound Identified | Interior % (AN) | Exterior % (AN) |
|---|---|---|
| Toluene | 0.72 | 0.62 |
| Hexanol, N | 0.10 | — |
| Methyl-2-Methyl Butyrate | — | 0.07 |
| 1,3,5-Heptatriene | — | 0.02 |
| Furfural | Trace | — |
| Aldehyde C-6 | — | 0.03 |
| Ethyl Butyrate | — | 0.04 |
| Tetrachloroethylene | 0.06 | 0.01 |
| Ethyl-2-Methyl Butyrate | Trace | 0.22 |
| Ethyl Isovalerate | Trace | 0.22 |
| Xylene (Isomers) | 0.20 | 0.10 |
| 5-Hexenal, 4-Methylene | Trace | 0.04 |
| Styrene | Trace | 0.01 |
| Nonane, N | Trace | — |
| Benzaldehyde | 0.01 | 0.03 |
| Alpha Pinene | 1.37 | 1.00 |
| Phenol | Trace | 0.01 |
| Beta Phellandrene | 0.05 | 0.02 |
| Beta Pinene | 6.31 | 4.83 |
| Myrcene | 20.61 | 21.18 |
| Alpha Phellandrene | 0.25 | 0.47 |
| Para Cymene | 0.31 | 0.48 |
| Limonene | 65.09 | 63.01 |
| Gamma Terpinene | — | 0.04 |
| Alpha, Para Dimethyl Styrene | 0.22 | 0.40 |
| Terpinolene | 0.02 | 0.47 |
| Para Cresol | 0.02 | 0.01 |
| Homo Ocimene | Trace | 0.01 |
| 4-Isopropyl-2-Cyclohexen-1-One | — | 0.09 |
| Para-Menthe-8-ene-Epoxide | — | 0.16 |
| Cyclohexene, 4-Acetyl-1-Methyl | Trace | — |
| Citronellal | — | 0.02 |
| Ethyl Benzoate | — | Trace |
| Para Methyl Acetophenone | Trace | Trace |
| 4-Isopropyl-2-Cyclohexen-1-One | Trace | 0.25 |
| 8-Cymenol | Trace | 0.10 |
| Myrtenal | Trace | 0.10. |
| Estragole | — | Trace |
| Alpha Terpineol | Trace | 0.05 |
| Neral | Trace | 0.13 |
| Carveol | 0.05 | 0.09 |
| Cuminyl Aldehyde | 0.01 | — |
| Isopropyl Benzaldehyde, Para | 0.10 | 0.10 |
| Thymol Methyl Ether | 0.37 | 0.53 |
| Para Mentha-1,8 Diene-3-One | — | 0.02 |
| Perillaldehyde | 0.01 | 0.02 |
| 1,5-Cyclohexadiene-1-Methanol, 4-(1-Methyl, Ethyl) | — | 0.03 |
| 2-Allyl-3,4(or 5)-Dimethyl-2-Cyclopenten-1-One | — | 0.01 |
| Anethole | — | 0.01 |
| Cuminyl Alcohol | — | 0.01 |
| Carvacrol | 0.01 | — |
| Bornyl Acetate | 0.12 | 0.11 |
| Myrtenal Acetate | 0.02 | 0.01 |
| Citronellyl Acetate | 0.07 | 0.13 |
| Neryl Acetate | Trace | 0.01 |
| Longipinene | 0.11 | 0.32 |
| Geranyl Acetate | 0.05 | 0.12 |
| Alpha Y Angene | 0.02 | 0.10 |
| Longicyclene | 0.01 | 0.06 |
| Sativen | 0.02 | 0.09 |
| Longifolene Isomer | 0.01 | 0.02 |
| Longifolene | 0.39 | 1.31 |
| Bergamotene | Trace | 0.05 |
| Beta Selinene | — | 0.01 |

-continued

| Compound Identified | Interior % (AN) | Exterior % (AN) |
|---|---|---|
| Beta Caryophyllene | — | 0.06 |
| Beta Bisabolene | Trace | 0.18 |
| Benzyl Salicylate | — | Trace |
| Hexadecanol | — | Trace |
| | 96.71 | 97.66 |

What is claimed is:

1. A process for quantitatively and qualitatively substantially continuously analyzing the aroma emitted and rate of emission of the components thereof:
   (i) from within the inner wood section and/or pith section; and
   (ii) from the outer tree bark surface of
a living tree simultaneously consisting essentially of the steps of:
   (a) providing at least one living tree having a trunk or tree limb located on a given central axis, said trunk or tree limb having an outer surface, a substantial portion of which is located at a given distance, "h" from said central axis and encompassed by said outer tree bark surface;
   (b) removing at least one depth core section from said inner volume running from said outer surface to a depth of from about "$\frac{1}{2}$" up to "h" into said inner volume along a directional vector "V" extending substantially radially frmo said central axis to said outer tree bark surface within said inner volume, said depth core section having an effective diameter $D_1$ equal to $2 \times$(effective radius, $R_1$) and a core section volume ranging from about $$[\pi R_1^2 h];$$

down to about $$\left[\frac{\pi R_1^2 h}{2}\right]$$

thereby forming at least one core section void within said living tree trunk or tree limb; then
   (c)-1: providing first analytical apparatus means comprising first trapping tube means attached to first negative pressure pump means associated with first chemical analysis means;
   (c)-2: providing second analytical apparatus means comprising a second trapping tube means attached to second negative pressure pump means associated with second chemical analysis means:
   (d) providing a hollow flexible enclosure means having an inner enclosure means void and an outer enclosure means surface encompassing said void and terminating at an enclosure rim means, said void being defined by said outer enclosure means surface and said enclosure rim means, an insertion orifice extending from said outer enclosure means surface to said inner enclosure means void, said enclosure means being capable of sealably gripping an unbroken portion of said outer tree bark surface of said living tree at said enclosure rim means;
   (e) causing said enclosure means to sealably grip said portion of said outer tree bark surface of said living tree at said enclosure rim means;
   (f) inserting said first trapping tube means into said core section void along said directional vector "V";
   (g) inserting said second trapping tube means through said insertion orifice, causing it to be extended into said enclosure means void;
   (h) simultaneously engaging said first negative pressure pump means and said second negative pressure pump means whereby components of the aroma evolving from said outer tree bark surface of said living tree are entrapped in said second trapping tube means and components of the aroma evolving from within said living tree are entrapped in said first trapping tube means, simultaneously; and
   (j) analyzing the contents of said first trapping tube means using said first chemical analysis means and said second trapping tube means using said second chemical analysis means substantially continuously and substantially simultaneously.

2. Apparatus for quantitatively and qualitatively substantially continuously analyzing the aroma evolved:
   (i) from within the inner wood section and/or pith section; and
   (ii) from the outer tree bark surface of
a living tree, simultaneously, consisting essentially of:
   (a) at least one living tree trunk or tree limb located on a given central axis having an outer tree bark surface, a substantial portion of which is located at a given distance, "h" from said central axis; an inner volume surrounding said central axis and encompassed by said outer tree bark surface; a depth core section removed from said inner volume running from said outer tree bark surface to a depth of from about "$\frac{1}{2}$h" up to "h" into said inner volume along a directional vector "V" extending substantially radially from said central axis to said outer tree bark surface within said inner volume, said depth core section having an effective diameter $D_1$ equal to $2 \times$(effective radius, $R_1$) and a core section volume ranging from about $$[\pi R_1^2 h];$$

down to about $$\left[\frac{\pi R_1^2 h}{2}\right]$$

thereby forming a core section void within said living tree;
   (b)-1: first analytical apparatus means comprising first trapping tube means attached to first negative pressure pump means associated with first chemical analysis means;
   (b)-2: second analytical apparatus means comprising second trapping tube means attached to second negative pressure pump means associated with second chemical analysis means;
   (c) hollow flexible enclosure means having an inner enclosure means void and an outer enclosure means surface encompassing said void and terminating at an enclosure rim means, said void being defined by said outer enclosure means surface and said enclosure rim means, an insertion orifice extending from said outer enclosure means surface to said inner enclosure means void, said enclosure means sealably gripping an unbroken portion of said outer tree bark surface of said living tree at said enclosure rim means;

(d) said first trapping tube means being inserted into said core section void along said directional vector "V";

(e) said second trapping tube means being inserted through said insertion orifice, causing it to be extended into said enclosure means void;

whereby when said first negative pressure pump means and said second negative pressure pump means are simultaneously engaged, components of the aroma evolving from said outer tree bark surface of said living tree are entrapped in said second trapping tube means and components of the aroma evolving from within said living tree are entrapped in said first trapping tube means, simultaneously, enabling the contents of said first trapping tube means and said second trapping tube means to be continuously analyzed substantially simultaneously using said first and second chemical analysis means.

3. The apparatus of claim 2 wherein the hollow flexible enclosure means is a hemispherically-shaped cup means having an inner cup means void and an outer cup means surface surrounding said void and terminating at a substantially circular rim of radius $R_2$, with the inner volume of said cup means being about $$[\tfrac{2}{3}\pi R_2^3].$$

4. The process of claim 1 wherein the living tree is a living Douglas Fir.

5. The apparatus of claim 2 wherein the living tree is a living Douglas Fir.

6. The process of claim 1 wherein:
(a) the living tree is bearing living fruit; and
(b) the outer surface and the inner volume of the living fruit are analyzed simultaneously with the analysis of the outer tree bark surface and inner wood section and/or pith section of the living tree.

7. Apparatus of claim 2 for quantitatively and qualitatively substantially continuously and simultaneously analyzing the aroma evolved:
(i) from within the inner wood section and/or pith section; and
(ii) from the outer tree bark surface of a living tree; and
(i') from within; and
(ii') from the outer surface of
a living fruit borne by said living tree, simultaneously consisting essentially of:
(a) at least one living tree trunk or tree limb located on a given central axis having an outer tree bark surface, a substantial portion of which is located at a given distance, "h" from said central axis; an inner volume surrounding said central axis and encompassed by said outer tree bark surface; a depth core section removed from said inner volume running from said outer tree bark surface to a depth of from about "½h" up to "h" into said inner volume along a directional vector "V" extending substantially radially from said central axis to said outer tree bark surface within said inner volume, said depth core section having an effective diameter $D_1$ equal to 2×(effective radius, $R_1$) and a core section volume ranging from about $$[\pi R_1^2 h]$$

down to about $$\left[\frac{\pi R_1^2 h}{2}\right]$$

thereby forming a core section void within said living tree;

(b)-1: first analytical apparatus means comprising first trapping tube means attached to first negative pressure pump means associated with first chemical analysis means;

(b)-2: second analytical apparatus means comprising second trapping tube means attached to second negative pressure pump means associated with second chemical analysis means;

(c) hollow flexible enclosure means having an inner enclosure means void and an outer enclosure means surface encompassing said void and terminating at an enclosure rim means, said void being defined by said outer enclosure means surface and said enclosure rim means, an insertion orifice extending from said outer enclosure means surface to said inner enclosure means void, said enclosure means sealably gripping an unbroken portion of said outer tree bark surface of said living tree at said enclosure rim means;

(d) said first trapping tube means being inserted into said core section void along said directional vector "V";

(e) said second trapping tube means being inserted through said insertion orifice, causing it to be extended into said enclosure means void; and in addition:

(a') a living fruit borne by said living tree located on a given central axis having an outer surface, a substantial portion of which is located at a given distance, "$h_F$" from said central axis; an inner volume surrounding said central axis and encompassed by said outer surface; a depth core section removed from said inner volume running from said outer surface to a depth of from about "½$h_F$" up to "$h_F$" into said inner volume along a directional vector "$V_F$" extending substantially radially from said central axis to said outer surface within said inner volume, said depth core section having an effective diameter equal to 2×(effective radius $R_{12}$) and a core section volume ranging from about $$[\pi R_{12}^2 h_F]$$

down to about $$\left[\frac{\pi R_{12}^2 h_F}{2}\right]$$

thereby forming a core section void within said living fruit;

(b')-1 third analytical apparatus means comprising third trapping tube means attached to third negative pressure pump means associated with third chemical analysis means;

(b')-2 fourth analytical apparatus means comprising fourth trapping tube means attached to fourth negative pressure pump means associated with fourth chemical analysis means;

(c') second hollow flexible enclosure means having an inner enclosure means void and an outer enclosure means surface encompassing said void and terminating at an enclosure rim means, said void being defined by said outer enclosure means surface and said enclosure rim means, an insertion orifice extending from said outer enclosure means surface to said inner enclosure means void, said enclosure means sealably gripping an unbroken portion of said outer surface of said living fruit at said enclosure rim means;

(d') said third trapping tube means being inserted into said core section void along said directional vector "$V_F$";

(e') said fourth trapping tube means being inserted through said insertion orifice, causing it to be extended into said enclosure means void of said second hollow flexible enclosure means;

whereby when said first, second, third and fourth negative pressure pump means are simultaneously engaged, components of the aromas evolved from said outer tree bark surface of said living tree are entrapped in said second trapping tube means; components of the aroma evolving from within said living tree are entrapped in said first trapping tube means; components of the aroma evolving from within one or more of the living fruits borne by said living tree are entrapped in said third trapping tube means; and components of the aroma evolving from the outer surface of one or more of the living fruits borne by said living tree are entrapped in said fourth trapping tube means, simultaneously, enabling the contents of said first, second, third and fourth trapping tube means to be continuously analyzed substantially simultaneously using said first, second, third and fourth chemical analysis means.

* * * * *